US006703614B1

(12) United States Patent
Stifter et al.

(10) Patent No.: US 6,703,614 B1
(45) Date of Patent: Mar. 9, 2004

(54) METHOD FOR DETERMINING THE DISTANCE OF A NEAR-FIELD PROBE FROM A SPECIMEN SURFACE TO BE EXAMINED, AND NEAR-FIELD MICROSCOPE (75) Inventors: Thomas Stifter, Illereichen (DE); Othmar Marti, Ulm (DE); Robert Brunner, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/442,429

(22) Filed: Nov. 17, 1999

(30) Foreign Application Priority Data

Nov. 17, 1998 (DE) .......................................... 198 52 833

(51) Int. Cl.$^7$ ................................................ G01B 5/28
(52) U.S. Cl. ........................ 250/306; 250/307; 73/105
(58) Field of Search ................................ 250/306, 310, 250/307; 73/105

(56) References Cited

U.S. PATENT DOCUMENTS

| 5,103,094 A | * | 4/1992 | Hayes et al. ............... 250/306 |
| 5,418,363 A | * | 5/1995 | Elings et al. ............... 250/306 |
| 5,489,774 A | * | 2/1996 | Akamine et al. ........... 250/234 |
| 5,503,010 A | * | 4/1996 | Yamanaka .................... 73/105 |
| 5,602,330 A | * | 2/1997 | Chamberlin et al. .......... 73/105 |
| 5,902,928 A | * | 5/1999 | Chen et al. .................... 73/105 |
| 6,167,753 B1 | * | 1/2001 | Chen et al. .................... 73/105 |

* cited by examiner

*Primary Examiner*—Jack Berman
*Assistant Examiner*—Anthony Quash
(74) *Attorney, Agent, or Firm*—Reed Smith LLP (57) ABSTRACT

A method for determining the distance of a scanning probe of a scanning probe microscope from a specimen surface to be examined comprising the steps of: exciting the scanning probe to oscillations lateral to a surface to be examined; recording at least one amplitude signal and a frequency signal and a phase signal of the oscillating scanning probe; superimposing a vertically oscillating movement of the scanning probe and specimen surface to be examined relative to one another is superimposed on the oscillation of the scanning probe lateral to the specimen surface to be examined; and determining the distance of the scanning probe from the specimen surface from at least one of the amplitude signal and a frequency signal and a phase signal.

21 Claims, 7 Drawing Sheets

METHOD FOR DETERMINING THE DISTANCE OF A NEAR-FIELD PROBE FROM A SPECIMEN SURFACE TO BE EXAMINED, AND NEAR-FIELD MICROSCOPE

BACKGROUND OF THE INVENTION a) Field of the Invention

The invention is directed to a method for determining the distance of a scanning probe of a scanning probe microscope from a specimen surface to be examined, wherein the near-field probe is excited to oscillations lateral to a specimen surface to be examined and at least one amplitude signal and/or frequency signal of the oscillating scanning probe is recorded.

In addition to the method for determining distance, the invention also provides a method for imaging the topography of a specimen surface and a scanning probe microscope, in particular an optical scanning probe microscope, which comprises at least one holder for a specimen surface to be examined and at least one device for exciting oscillating movements of the scanning probe at least in the plane of the specimen surface to be examined.

b) Description of the Related Art

The scanning probe microscopy family includes, for example, near-field microscopy (abbreviated SNOM: Scanning Near-field Optical Microscopy), scanning tunneling microscopy (STM), force microscopy (SFM), and scanning electrochemical microscopy (SECM). The method according to the present invention will be described more fully hereinafter with reference to near-field microscopy, although it should not be considered restricted thereto. It will be a simple matter for the person skilled in the art to transfer the general principles to different types of scanning probe microscopy. Optical near-field microscopy makes it possible to overcome the conventional diffraction-limited resolution limit and to examine structures that are far smaller than half of the wavelength of the utilized light.

For operation of an optical near-field microscope, a small aperture must be brought to within a few nanometers of the specimen surface to be examined. Light emitted from this aperture interacts with the specimen and can then be evaluated by means of suitable collection optics and a detector. A reversal of the light path (i.e., external illumination, collection of the light by the fiber) is also possible. An image is generated in that the probe (aperture) is moved over the surface point by point and line by line and the data obtained in so doing are evaluated electronically and compiled to form an image.

A type of probe used in near-field optics is a tapered glass fiber which is produced by etching and/or drawing and is coated with metal in such a way that only the area of the fibers at the very front remains permeable to light (aperture). With respect to these probes, reference is had to E. Betzig, J. K. Trautmann, T. D. Harris, J. S. Weiner and R. L. Kostelak, *Science* 257, 1468–1470 (1991), wherein the disclosure contained in this publication is incorporated in its entirety in the present Application.

The shear force detection method, for example, is used to determine the topography of the specimen surface and the distance between the probe and surface and to maintain regulation thereof constant during measurement. In this regard, reference is had to E. Betzig, P. L. Finn and J. S. Weiner, *Appl. Phys. Lett.* 60, 2484–2486 (1992) and R. Toledo-Crow, P. C. Yan, Y. Chen and M. Vaez-Iravani, *Appl. Phys. Lett.* 60, 2957–2959 (1992). The disclosure contained in these publications is incorporated in its entirety in the present Application.

In the shear force detection method, the glass fiber probe which is situated almost vertical to the surface is set in mechanical resonance, so that it executes lateral oscillations, i.e., oscillations parallel to the surface. The frequency range of the resonance is preferably between 10 kHz and 4000 kHz, depending on tip geometry. As the glass fiber tip approaches the surface, there occur at a distance of a few nanometers, preferably less than 30 nm, shear forces which act between the tip and the specimen and which cause a change in the amplitude and phase of the oscillation. The detected change in amplitude and/or frequency and/or phase can be used to regulate the distance between the probe and the surface or to determine the topography of the specimen surface.

Different detection methods have been developed for measuring the amplitude, frequency or phase of the tip oscillations; these methods can be distinguished as either optical or non-optical. With respect to optical detection methods, reference is had to E. Betzig, P. L. Finn and J. S. Weiner, *Appl. Phys. Lett.* 60, 2484–2486 (1992); R. Toledo-Crow, P. C. Young, Y. Chen and M. Vaez-Iravani, *AppL. Phys. Lett.* 60, 2957–2959 (1992); and R. D. Grober, T. D. Harris, J. K. Trautman, and E. Betzig, *Rev. Sci. Instrum.* 65, 626–631 (1994). For non-optical methods, reference is had to J. W. P. Hsu, Mark Lee and B. S. Deaver, *Rev. Sci. Instrum.* 66, 3177–3181 (1995); K. Karrai and R. D. Grober, *AppL. Phys. Lett.* 66, 1842–1844 (1995); J. Barenz, O. Hollricher and O. Marti, *Rev. Sci. Instrum.* 67, 1912–1916 (1996); R. Brunner, A. Bietsch, O. Hollricher, and O. Marti, *Rev. Sci. Instrum.* 68, 1769–1772 (1997). The disclosure contained in these publications is incorporated in its entirety in the present Application.

It has been shown that a drop in amplitude first appears at a distance of a few nanometers from the specimen, so that an interaction between the probe and surface that can be regulated first occurs in this range.

In order to obtain the topography of near-field optical imaging, regulation at constant shear force has always been used up to this point, i.e., the probe was located in the interaction range with respect to the surface during the entire duration of recording and measurement. Alternatively, in order to eliminate electrochemical reactions on the specimen surface, it was suggested that a constant distance be maintained between the specimen and probe tip. In this connection, reference is had to P. I. James, L. F. Garfias-Mesias, P. I. Moyer, W. H. Smyre, "Scanning Electrochemical Microscopy with Simultaneous Independent Topography", *J. Electrochem. Soc.* vol. 145, no. 4, pp L-64–L66, wherein the disclosure contained in this publication is incorporated in its entirety in the present Application.

Due to the fact that the probe is located in the range of interaction with respect to the surface during the entire measurement in the measuring and imaging process according to the prior art, the probe and specimen are also loaded by shear forces during the entire duration of recording. With soft specimens, this continual loading during measurement can lead to deformation or even complete destruction of the specimen or specimen surface. Aside from destruction of the specimen surface, the probe can also be damaged or rendered unusable due to the constant loading. These problems occur in particular when examining organic specimens, for example, soft polymers and biological specimens. In extreme cases, because of the problems described above, it is impossible to image the surfaces and topography of soft specimens of this kind.

OBJECT AND SUMMARY OF THE INVENTION

Accordingly, it is the primary object of the invention to provide a method and a device by which the disadvantages described above can be eliminated. In particular, an imaging method will be provided which also allows examination of soft specimens, especially the topography thereof, as well as a corresponding scanning probe microscope, especially an optical near-field microscope.

According to the invention, this object is met in a method for determining the distance of the scanning probe in that an oscillating movement of the scanning probe and specimen to be examined relative to one another is superimposed on the lateral oscillation of the scanning probe. The distance of the scanning probe from the specimen is then determined from the amplitude signals and/or frequency signals and/or phase signals obtained from the movements of the scanning probe.

In a first embodiment form of the invention, the specimen surface is stationary and the scanning probe oscillates vertically as well as laterally.

Alternatively, the scanning probe can be fixed vertically and the specimen surface oscillates vertically, for example, in that the holder on which the specimen is arranged is set in oscillation.

In an advantageous embodiment form, the vertically oscillating movement has a sinusoidal shape.

The amplitude of the vertically oscillating movement is preferably in the range of 10 nm to 1 $\mu$m and the frequency is in the range of 10 Hz to 10 kHz.

In a particularly preferable manner, the invention is applied in optical near-field microscopy without being limited thereto. With respect to the near-field tips in optical near-field microscopy, reference is had to J. Barenz, O. Hollricher and O. Marti, "An Easy-to-use Non-optical Shear-force Distance Control for Near-field Optical Microscopes", *Rev. Sci. Instrum.* 67 (5), (May 1996), pages 1912–1916, wherein the disclosure contained in this publication is incorporated in its entirety in the present Application.

In addition to the method for determining distance, the invention also provides a distance regulating method for a scanning probe microscope in which the distance between the probe and the specimen surface is determined in accordance with a method described above and the scanning probe is advanced toward the specimen until reaching a predetermined damping value and/or frequency value and is then moved away from it.

The method described above can also be used with appropriate evaluating electronics to image surface topographies. A method of this kind can include the following steps, for example:

First, a damping value $S_0$ of the laterally excited oscillation is determined at a starting point (0, 0) of the specimen for a distance $d_0$ (0, 0) of the specimen probe from the specimen surface without vertically oscillating movement of the specimen probe;

the specimen probe is excited to vertically oscillating movement and the specimen surface is scanned point by point (x, y);

the damping $S_T$ of the specimen probe is determined for every specimen point (x, y) as the vertically oscillating movement traverses a predetermined specimen distance $d_T$;

when $S > S_0$, the distance $d_0$ (x, y) between the specimen probe and specimen surface is increased;

when $S_T = S_0$, the distance $d_0$ (x, y) is maintained constant, so that $d_0$ (x, y), which is determined in this way, reproduces the surface topography of the specimen.

The invention also provides an optical scanning probe microscope which has a scanning probe, at least one holder for a specimen surface to be examined, and at least one device for exciting oscillating movements of the scanning probe in the plane of the specimen surface to be examined (lateral oscillations) as well as vertical thereto (vertical oscillations).

In a particularly preferred manner, the scanning probe microscope has at least one piezo element for exciting the vertically oscillating movement. It is possible to excite the topography balance or topography compensation as well as the oscillation vertical to the specimen surface to be examined with only one piezo element.

In an improved, further-developed embodiment form, the periodic vertical modulation and topography compensation can be carried out by means of two separate piezo systems.

In order to be able to regulate and/or control the distance between the specimen probe and the specimen surface, it is provided in a further development of the invention that an amplitude damping of the lateral oscillation is predetermined, for example, by means of an electronic circuit, wherein the periodic change in the distance between the probe and surface may not exceed this amplitude damping. The laterally oscillating probe and the specimen then come closer to one another periodically until a predetermined amplitude damping is reached. Subsequently, they move away from each other again.

In the following, the invention will be described by way of example with reference to the drawings.

DESCRIPTION OF THE PREFERRED EMBODIMENTS

Figure 1:
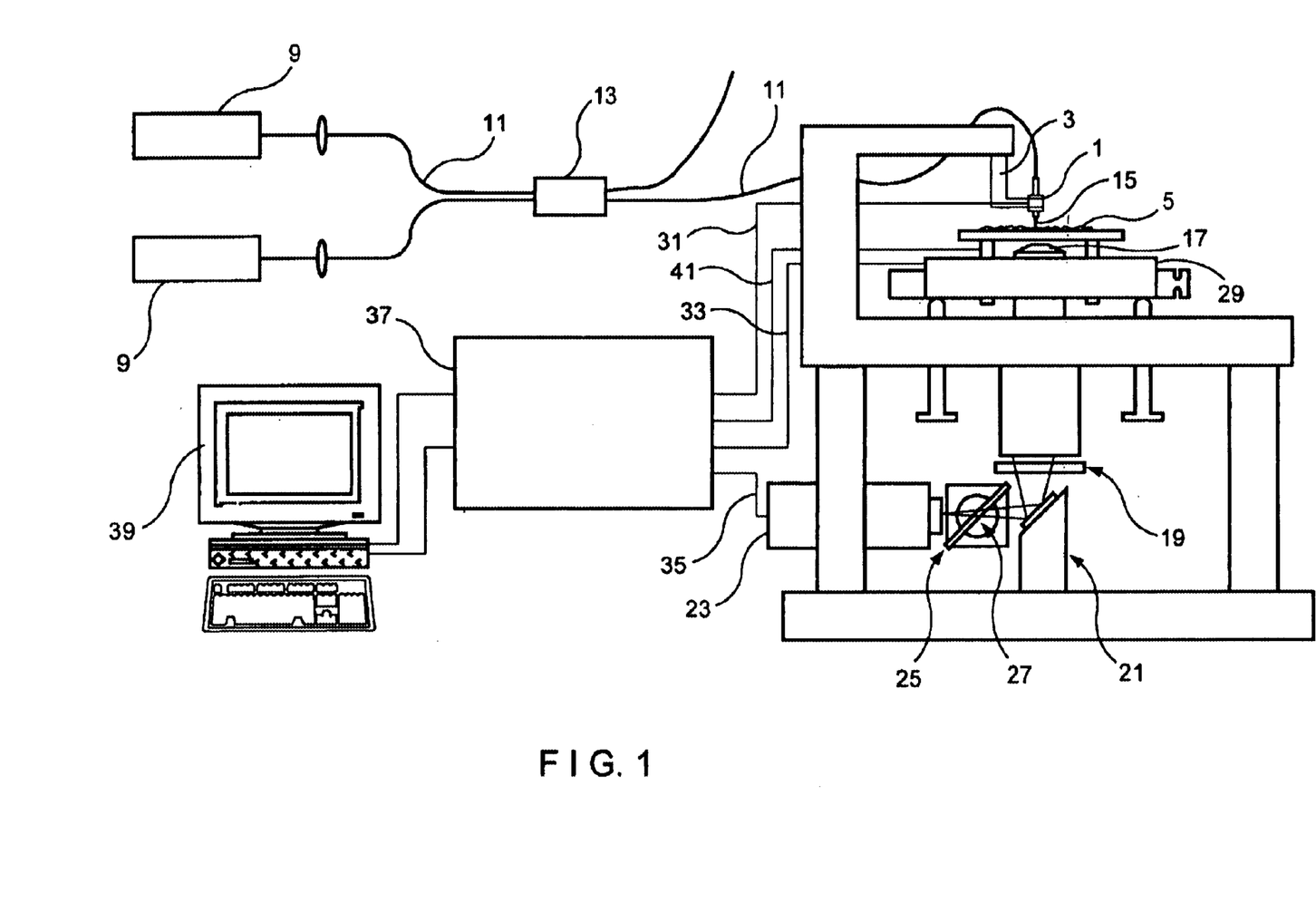
FIG. 1 shows the basic construction of an optical near-field microscope.

FIG. 1 shows the basic construction of an optical near-field microscope by way of example for a scanning probe microscope without the invention being limited thereto. The invention is applicable to every kind of scanning probe microscopy enabling a vertical movement of the scanning probe, for example, also electrochemical scanning probe microscopy with a thin capillary as is described in P. I. James, L. F. Garfias-Mesias, P. J. Moyer, W. H. Sruyre, "Scanning Electrochemical Microscopy with Simultaneous Independent Topography", op. cit.

The optical near-field microscope shown in FIG. 1 comprises a near-field probe 1 which is constructed in the present case as a thin glass fiber tip and is held by an arm 3. The specimen 5 can be examined by means of the near-field optical probe 1 in the observation position shown in the drawing.

Light sources for the near-field optical examination are lasers 9 which emit monochromatic light of a determined wavelength, for example, in the case of a He-Ne laser, red light with a wavelength of 633 nm.

This light is guided to the probe tip 15 via light waveguides 11 and a fiber coupler 13 and is emitted at the probe tip 15.

The light transmitting through the specimen 5 is collected by the objective 17, guided via the filter 19 and mirror 21 to the photodiode 23 in the position of the tilting mirror 25 in the position shown in dashed lines.

By swiveling the tilting mirror, the beam path can be guided to the CCD camera 27 instead of to the detection diode 23. The CCD camera 27 can be used for adjustment of optics, for characterization of the tips and for selection of a suitable specimen section.

A scanning of the specimen in the x-y direction, i.e., laterally, can be carried out, for example, as described above, by means of a piezo stage or table having piezo elements 29 for displacement of the specimens in the x- and y-directions. The scanning area of the piezo table in the x-y plane is, e.g., 100×100 $\mu$m in the present embodiment form. In order to compensate for piezo hysteresis effects, the table is regulated capacitively. The lateral resolution is, e.g., 0.5 nanometers. The shear force detection signal of the near-field tip is transmitted to the measuring unit 37 via line 31, the signal for the displacement in the x-y direction is transmitted to the measuring unit 37 via line 33, and the light signal recorded by the detection diode 23 is transmitted to the measuring unit 37 via line 35. The measuring unit 37 can have a function generator, a lock-in amplifier, a shear force regulator, a piezo control and an A-D/D-A card. The control of the individual measuring devices is carried out by means of a microcomputer 39 in which the scanned data are compiled to form an image. When an optical near-field microscope is used, as was described above, the image comprises an optical signal which is recorded by the CCD camera as well as topographical information which is determined by means of the method according to the invention which will be described in the following. The scanning speed for recording the image is at least 0.1 line/s; speeds of 10 lines/s can advantageously be achieved.

In addition to the embodiment form of the invention shown herein, in which light passing through the specimen, i.e., transmitted light, is recorded as an optical signal, it is also possible to record light reflected from the specimen as an optical signal or to use other types of scanning probes for detecting, e.g., an electrochemical signal or a force signal without departing from the concept of the invention. The embodiment form, shown herein, of a near-field optical microscope is therefore meant only as an example and is not meant to be exclusive.

In particular, any type of scanning probe can be taken into consideration for modulation of the tip in the z-direction which is described hereinafter with reference to FIGS. 2 to 3. The signal for modulation in the z-direction, i.e., the vertical movement of the near-field probe, from which the topography of the specimen surface is determined is transmitted via line 41 to the measuring unit 37.

Figure 2:
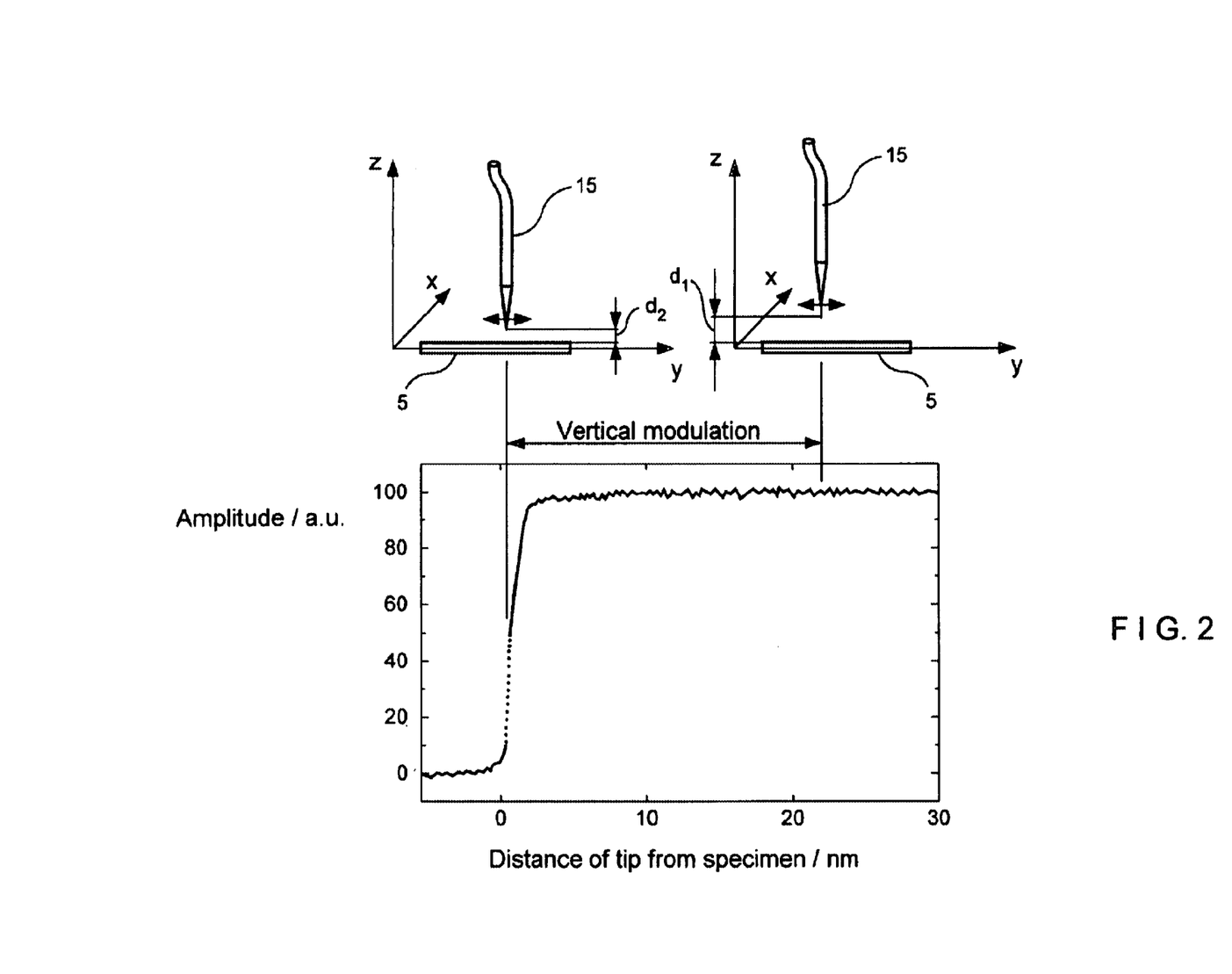
FIG. 2 shows an example of a scanning probe microscope, amplitude damping of the lateral oscillation of the scanning probe depending on the distance between the scanning probe and specimen surface.

FIG. 2 shows the amplitude of the laterally excited oscillation in the x-y plane as a function of the distance d of the tip 15, for example, the near-field tip 15 used by way of example for a scanning probe, from the specimen surface 5 in the z-direction. There are also similar dependencies for the shape of the frequency and phase of the laterally excited oscillation in the x-y plane. These dependencies can likewise be utilized for distance regulation or imaging of the surface topography according to the invention.

As can be seen from FIG. 2, the oscillation amplitude is sharply damped at a slight distance of the tip from the surface of the specimen 5, for example, at distance $d_2$ shown in FIG. 2, and, because of the damping, amounts to only 60% of the value of the amplitude with the tip at infinity.

If the tip is moved very far away from the specimen as is shown at right in FIG. 2, a damping of the lateral oscillation does not take place; the amplitude signal is approximately 100% of the value with the tip at a distance of infinity. In the method according to the invention, the specimen can now be moved back and forth periodically between the two positions shown in FIG. 2, that is, the position at distance $d_2$ from the specimen surface and the second position at distance $d_1$ from the specimen surface. Sinusoidal vertical oscillations are particularly suitable for this purpose.

The actual duration of interaction between the probe and specimen during the measurement operation is accordingly very sharply reduced, so that the loading of the specimen surface by the imaging process is substantially reduced compared with previously used methods. By actual duration of interaction is meant the time during which the probe, in this case the optical near-field tip, is located at a distance from the specimen within which a decrease in the lateral oscillation amplitude occurs. The oscillating movement vertical to the specimen surface, i.e., in the z-direction in the embodiment examples shown herein, is not limited to pure sinusoidal oscillations; rather, the invention includes any type of periodic movement of the tip toward and away from the specimen surface. The area shown in FIG. 2 is preferably traversed with a periodic movement in the frequency range of approximately 10 Hz to 10 kHz and with an amplitude of 10 nm to 1 $\mu$m.

The periodic change in distance between the probe and specimen can be realized by means of very different embodiment forms of a scanning probe microscope. Four examples of such embodiment forms are shown in FIGS. 3A to 3D.

Figure 3A:
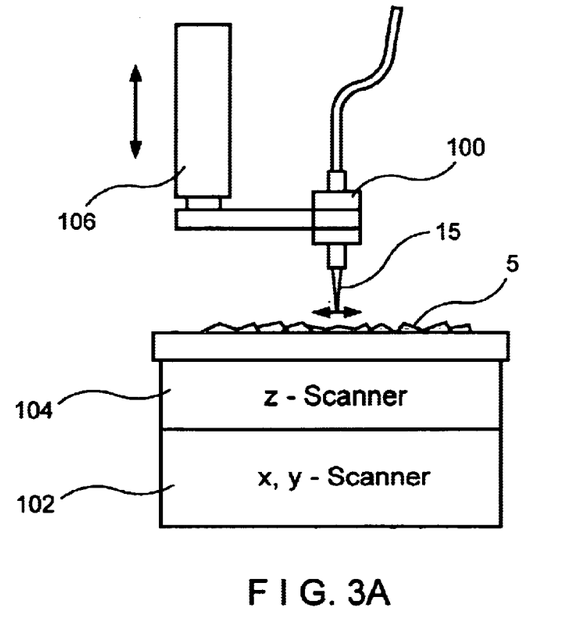
FIG. 3A shows a first embodiment form of the implementation of the invention with two piezo systems.

FIG. 3A shows an embodiment form of the invention in which a piezo system serves for displacement of the specimen in the z-direction for topography compensation and a second system carries out the vertical oscillation.

The specimen surface has a determined vertical profile or a determined topography which is to be imaged by means of optical near-field microscopy. For this purpose, the specimen tip is excited to lateral oscillations in the x-y plane. The distance of the specimen tip from the specimen surface is determined by means of a shear force detection device 100. The scanning of the specimen in the x-y direction is carried out by means of an x-y scanner which can be arranged at the specimen table itself. The topography compensation which is necessary in order to be able to image the specimen surface is carried out by means of a piezo system 104 which is likewise arranged at the specimen table. The piezo system 106, by which the near-field tip according to the invention is periodically moved toward and away from the specimen surface as is described in detail with reference to FIG. 2, is separate from piezo system 104.

Figure 3B:
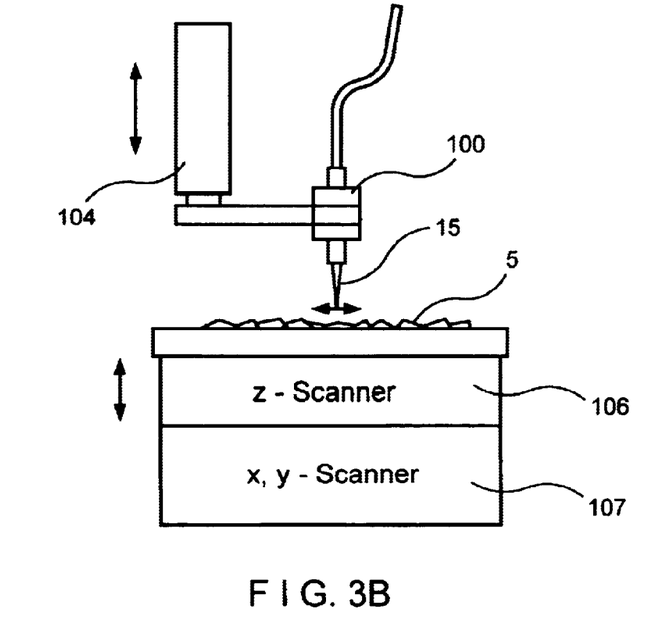
FIG. 3B shows a second embodiment example of the implementation of the invention with two piezo systems.

FIG. 3B shows an alternative embodiment form of the invention. The piezo system for topography compensation is now arranged directly at the tip, whereas the piezo system for vertical modulation is arranged at the specimen table; that is, in contrast to FIG. 3A, the periodic movement is now generated in that, instead of the tip, the table is moved relative to the tip.

In FIG. 3B, structural component parts identical to those in FIG. 3A have the same reference numbers.

Figure 3C:
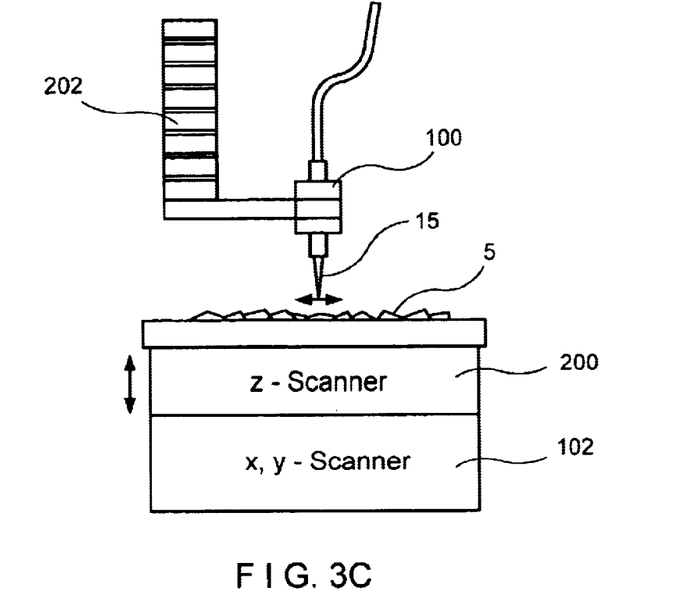
FIG. 3C shows a third embodiment form of the invention with one piezo system.
Figure 3D:
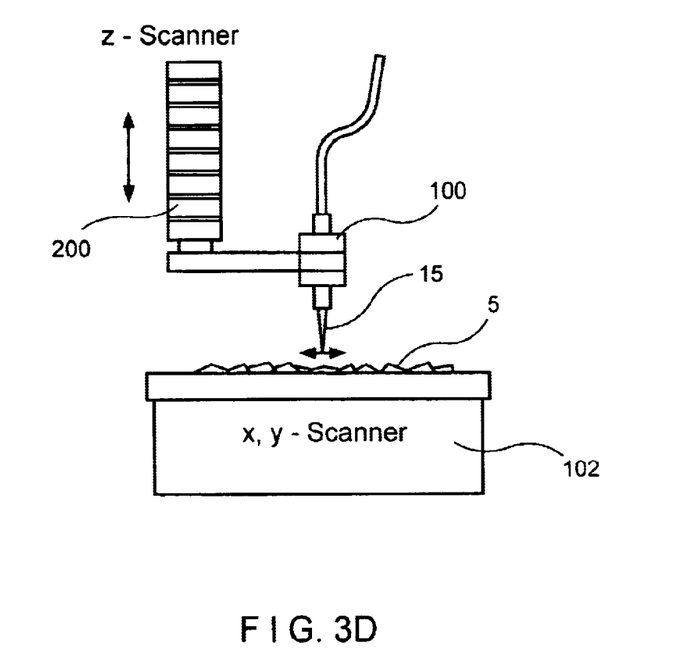
FIG. 3D shows a fourth embodiment form of the invention with one piezo system.

FIGS. 3C and 3D show embodiment forms of the invention in which the periodic vertical modulation and the topography compensation can be carried out by means of one and the same piezo system.

In FIGS. 3C and 3D, structural component parts identical to those in the embodiment forms shown in FIGS. 3A and 3B have the same reference numbers. In FIG. 3C, the shared piezo system for vertical modulation and topography compensation is integrated in the specimen table and designated by reference number 200. The scanning probe, in the present case the near-field tip, is fastened to the stationary arm 202; a movement in the direction of the tip and away from the tip is carried out only by means of the specimen table.

FIG. 3D shows an alternative embodiment form of the invention with only one piezo system.

In this case, the piezo system 200 for vertical modulation and topography compensation is arranged at the arm of the scanning probe, in the present case the near-field tip, and the specimen table is stationary in the z-direction. In this case, only the tip is moved relative to the specimen in the z-direction.

In a scanning probe microscope according to the invention, as is shown in FIGS. 3A to 3D, a possibility for distance regulation and, therefore, for topographic imaging of the specimen surface consists in that an amplitude damping of the lateral oscillation is predetermined by means of an electronic circuit, wherein this amplitude damping may not be exceeded by the periodic change in distance between the probe and surface. The laterally oscillating probe and the specimen are advanced toward one another periodically until a predetermined amplitude damping is reached. An alternative method will be described with reference to FIGS. 4 and 5.

Figure 4:
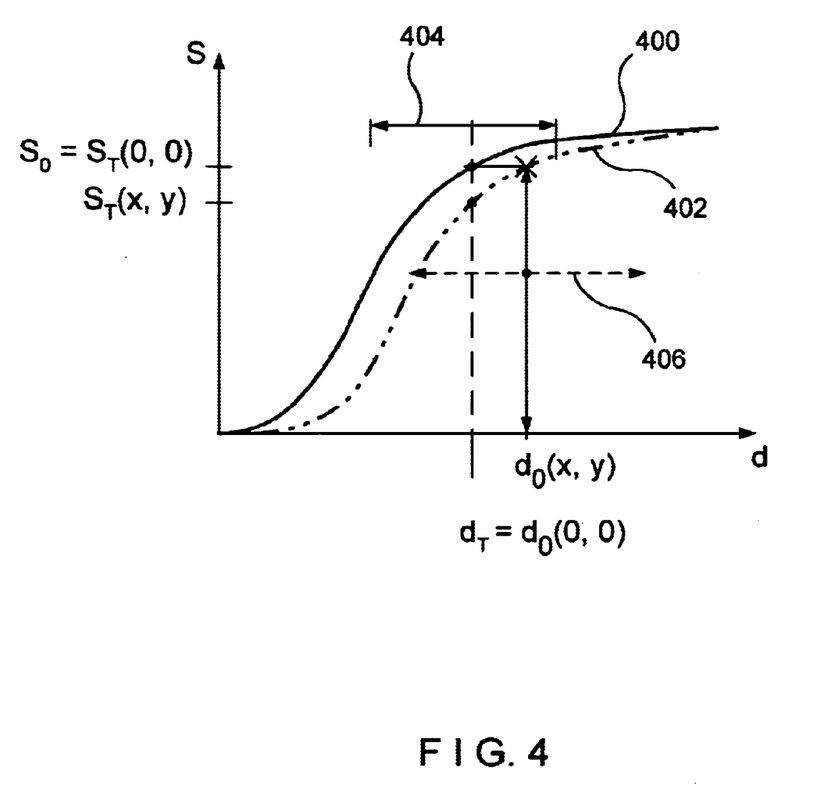
FIG. 4 shows an amplitude damping of the lateral oscillations of the specimen tip depending on the specimen location.

The dependencies of the amplitude signal S of the laterally excited oscillation in the x-y direction on the specimen distance d are indicated in FIG. 4 for two different specimen locations. Curve 400 describes the dependency at starting point (0, 0); curve 402 describes the dependency at another optionally selected location (x, y) on the specimen.

A vertical oscillation 404 is excited at location (0, 0) proceeding from distance $d_0$ (0, 0) of the scanning probe from the specimen surface. The oscillation amplitude $S_T$ (0, 0) is determined at a distance $d_T$ which corresponds in the present case to time point T of the zero crossover of the oscillation and, therefore, to distance $d_0$ (0, 0). When this oscillation amplitude $S_T$ (0, 0) coincides with a predetermined value $S_0$, the tip remains at distance $d_0$. The tip is now moved to location x, y for scanning the specimen. Due to a different height of the specimen, curve 402 results for the shape of the oscillation amplitude. Oscillation amplitude $S_T(x, y)$ results at distance $d_T$ when a vertical oscillation 404 is excited such as at location (0, 0). If $S_T(X, Y)$ is less than $S_0(0, 0)$, as in the present embodiment example, the tip is lifted, i.e., moved away from the specimen. In position x, y, the scanning probe, in the present case the near-field tip, is located at a distance $d_0(x, y)$. A vertical oscillation 406 is now excited again. At time T of zero crossover, the oscillation amplitude corresponds to the predetermined value $S_0$.

Subsequently, another specimen location is scanned by the scanning probe and the regulating process described above is repeated. In this way, the topography of the specimen surface is obtained by determining $d_0(x, y)$ for all x, y on the specimen surface.

Figure 5:
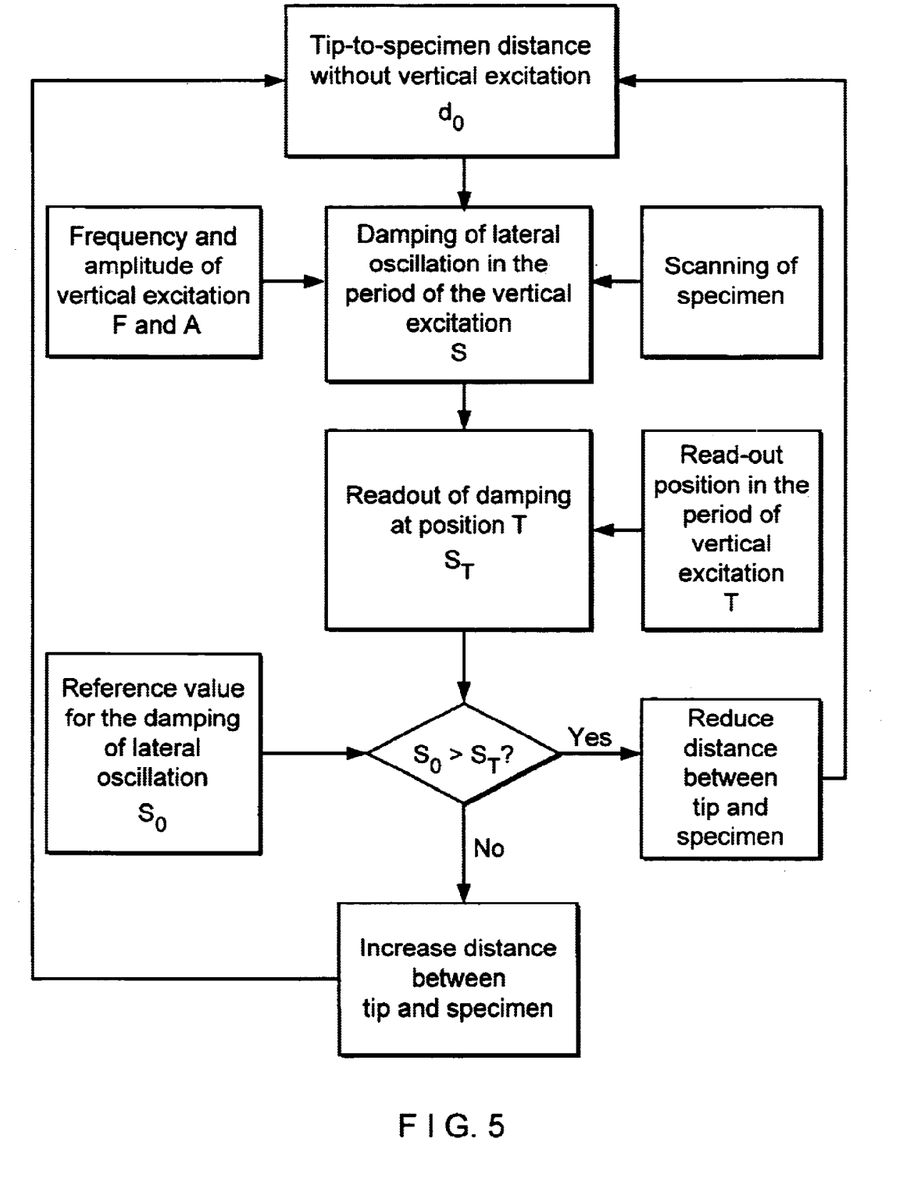
FIG. 5 shows a flow chart for a regulating procedure for determining the surface topography according to the invention.

The above-described embodiment form of the method according to the invention for determining the topography of the surface by vertically excited oscillations of the scanning probe and recording of the amplitude signal of the lateral oscillation are shown again in the flow chart in FIG. 5.

First, a distance $d_0$ of the scanning probe is adjusted without vertical excitation. A scanning of the specimen is then carried out; in so doing, the scanning probe is excited to vertical oscillation at a predetermined amplitude and frequency. The damping is determined from the amplitude signal or frequency signal or phase signal of the vertical oscillation at time T, for example, by setting a trigger signal in a lock-in amplifier. A comparison with the predetermined reference value $S_0$ for the damping of the lateral oscillation is then carried out. This reference value can again be an amplitude value, a frequency value or a phase value. If $S_0$ is less than $S_T$, the distance between the probe or tip and the specimen surface is reduced. If $S_0$ is greater than $S_T$, it is increased. If $S_0$ is equal to $S_T$, the distance is left unchanged.

The topography of the specimen surface is given by $d_0(x, y)$ which is determined in the manner indicated above.

Figure 6:
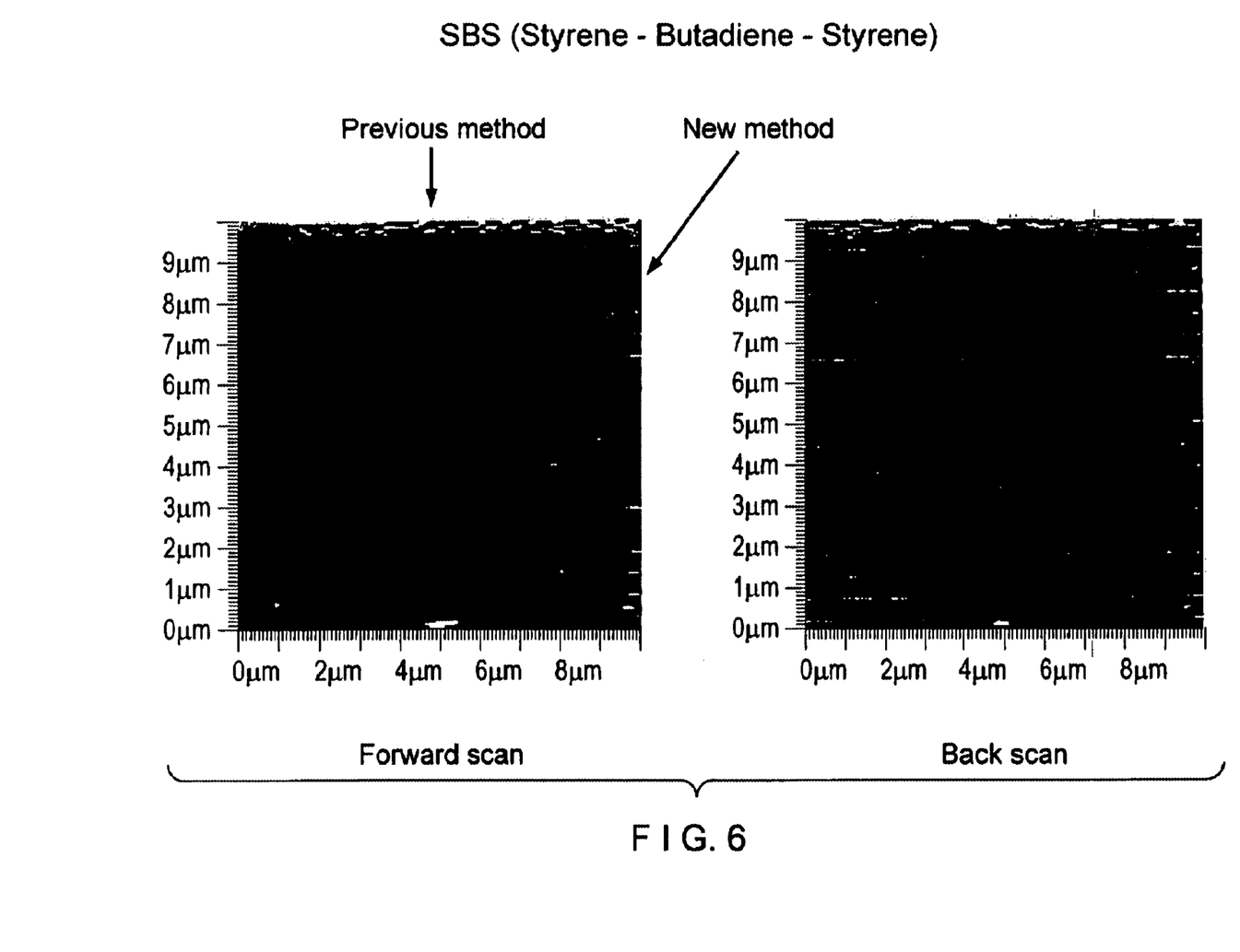
FIG. 6 shows imaging of a styrene-butadiene-styrene surface with an imaging method according to the invention.

Results for the novel device and the novel method for scanning probe microscopy are shown in FIG. 6.

A near-field microscope which can be used for recording imaging according to FIG. 6 is described in R. Brunner, "Development of an Optical Near-field Microscope for Examination of Biological Specimens [Entwicklung eines optischen Nahfeldmikroskopes zur Untersuching biologischer Proben]" (doctoral dissertation in Natural Sciences, University of Ulm, 1998), wherein the disclosure contained therein is incorporated in its entirety in the present Application. A piezoelectric system for shear force measurement is used in this microscope. The specimen shown in FIG. 6 is a styrene-butadiene-styrene polymer. The topography of this polymer could not be imaged by the conventional method of shear force regulation because the surface was blurred by the constant interaction with the probe. It is now possible by means of the novel imaging method to resolve both the topographical and optical structures of this specimen.

As was stated above, the periodic change in the distance between the probe and the surface can also be used in scanning probe microscopy methods other than near-field optics, for example, in force microscopy and/or in electrochemical microscopy.

While the foregoing description and drawings represent the preferred embodiments of the present invention, it will be obvious to those skilled in the art that various changes and modifications may be made therein without departing from the true spirit and scope of the present invention.

What is claimed is:

1. A method for determining the distance of a scanning probe of a scanning probe microscope from a specimen surface to be examined, comprising the following steps:

exciting the scanning probe to oscillations lateral to a surface to be examined;

recording at least one of an amplitude signal and a frequency signal and a phase signal of the laterally oscillating scanning probe;

superimposing a vertically oscillating movement of the scanning probe and specimen surface to be examined relative to one another on the oscillation of the scanning probe lateral to the specimen surface to be examined; and determining the distance of the scanning probe from the specimen surface from the recorded signal of the laterally oscillating scanning probe.

2. The method according to claim 1, wherein the specimen surface is stationary and the scanning probe oscillates vertically relative to the latter.

3. The method according to claim 1, wherein the scanning probe is fixed vertically and the specimen oscillates vertically.

4. The method according to claim 1, wherein the vertically oscillating movement is sinusoidal.

5. The method according to claim 1, wherein the amplitude of the vertically oscillating movement is in the range of 10 nm to 1 μm.

6. The method according to claim 1, wherein the frequency of the vertically oscillating movement is in the range of 10 Hz to 10 kHz.

7. The method according to claim 1, wherein the scanning probe is an optical near-field tip.

8. A distance regulating method for an optical scanning probe microscope, wherein the distance of the probe from the specimen surface is determined by a method according to claim 1, including the step of advancing scanning probe toward the specimen until at least one of a predetermined amplitude value and frequency value and phase value is reached and is then moved away from it.

9. The method according to claim 1, wherein the scanning probe is an optical near-field probe for optical near-field microscopy.

10. A method for imaging the specimen surface and the specimen topography by scanning probe microscopy, comprising the steps of:

exciting a scanning probe of a scanning probe microscope to oscillations lateral to the surface, the lateral oscillations of the scanning probe being used to measure the distance of the scanning probe from the specimen surface; and superimposing an oscillating movement of the scanning probe vertical to the specimen surface and in the vertical direction on the lateral movement of the scanning probe.

11. The imaging method according to claim 10, wherein the specimen surface is stationary and the scanning probe oscillates vertically.

12. The imaging method according to claim 10, wherein the scanning probe is fixed vertically and the specimen surface oscillates vertically.

13. The imaging method according to claim 10, wherein the vertically oscillating movement is sinusoidal.

14. The imaging method according to claim 10, wherein the amplitude of the vertically oscillating movement is in the range of 10 nm to 1 μm.

15. The imaging method according to claim 10, wherein the frequency of the vertically oscillating movement is in the range of 10 Hz to 10 kHz.

16. The imaging method according to claim 10, further including the step of advancing the scanning probe toward the specimen until at least one of a predetermined amplitude value and frequency value and phase value is reached and is then moved away from it.

17. A scanning probe microscope, especially near-field optical microscope, comprising:

at least one scanning probe;

at least one holder for a specimen surface to be examined;

at least one device for exciting lateral oscillating movements of the scanning probe to the plane of the specimen surface to be examined; and means for exciting oscillating movements vertical to the specimen surface to be examined; and wherein the near-field microscope comprises a regulating device for regulating the distance from the specimen surface to be examined by using the lateral oscillating movements of the scanning probe, wherein the distance of the probe from the specimen surface is determined by moving the scanning probe toward the specimen until at least one of a predetermined amplitude value and frequency value and phase value is reached and is then moved away from the specimen.

18. The microscope according to claim 17, wherein a device is provided for recording at least one of the amplitude signal and frequency signal of the forced oscillating movement depending on the distance of the scanning probe from the specimen surface.

19. The microscope according to claim 17, wherein the scanning probe comprises a near-field tip for optical near-field microscopy.

20. The microscope according to claim 17, wherein the device for exciting oscillating movements comprises at least one piezo element.

21. The microscope according to claim 20, wherein the means for exciting oscillating movements vertical to the specimen plane comprise a piezo element.

* * * * *